US00PP13757P29

(12) United States Plant Patent
Meilland

(10) Patent No.: US PP13,757 P2
(45) Date of Patent: Apr. 29, 2003

(54) FLORIBUNDA ROSE PLANT NAMED 'MEICINELLE'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 10/020,941

(22) Filed: Dec. 19, 2001

(51) Int. Cl.[7] ..... A01H 5/00
(52) U.S. Cl. ..... Plt./142
(58) Field of Search ..... Plt./142

*Primary Examiner*—Bruce R. Campell
*Assistant Examiner*—W C Haas
(74) *Attorney, Agent, or Firm*—Burns, Doane, Swecker & Mathis, LLP

(57) ABSTRACT

A new and distinct variety of Floribunda rose plant is provided which abundantly forms on a continuous basis semi-double blossoms that are red spotted with white in coloration. The plant exhibits a bushy and vigorous well-formed growth habit, and good resistance to *Marsonia rosae* and Phragmidium. The attractive very dense medium green foliage contrasts nicely with the blossom coloration. The new variety is particularly well suited for growing as attractive ornamentation in parks and gardens.

1 Drawing Sheet

BOTANICAL CLASSIFICATION

*Rosa hybrida.*

SUMMARY OF THE INVENTION

Figures 1, 2, 3, 4, 5, 6, 7, 8, 9, 10, 11, 12, 13, 14, 15:
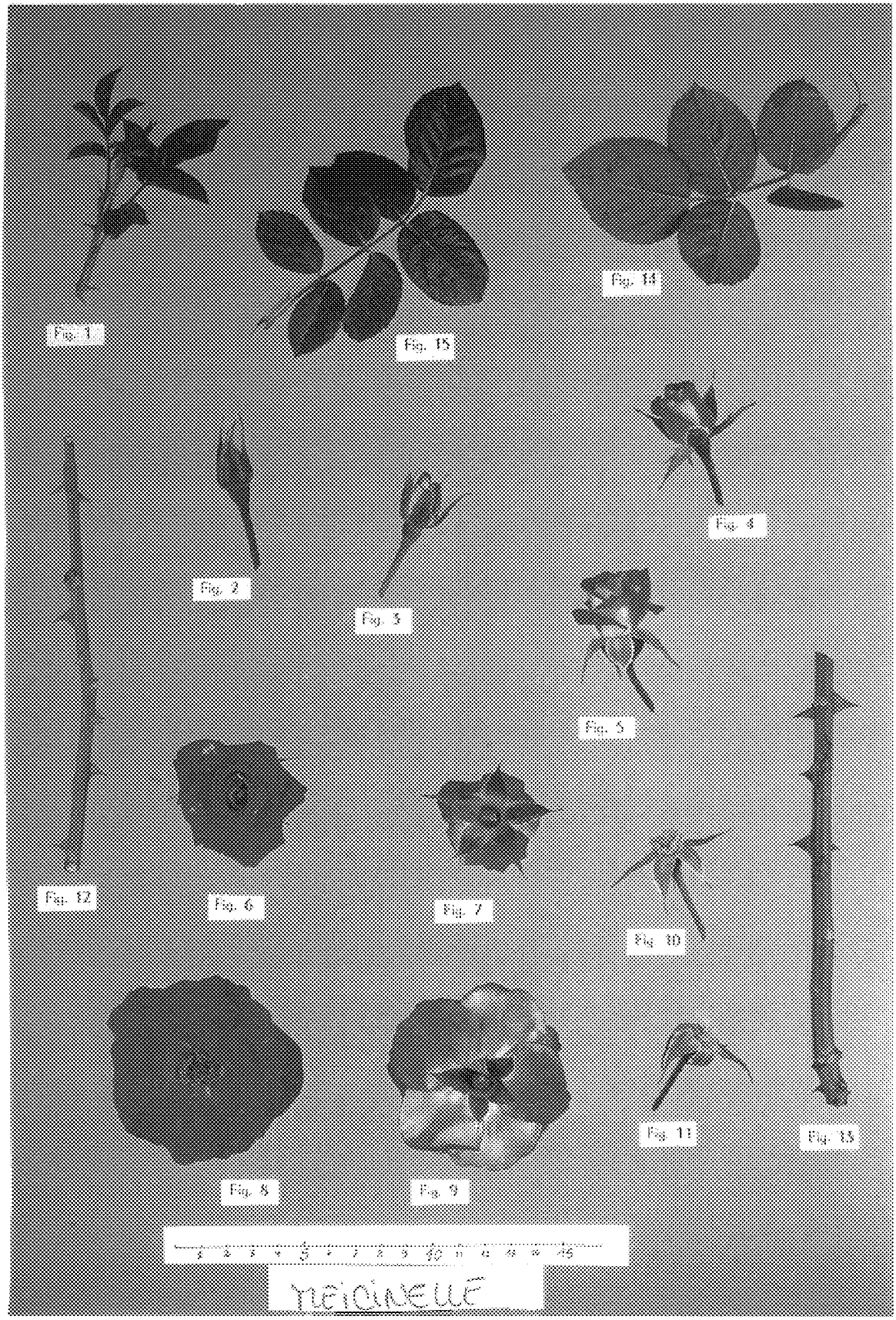

The new variety of *Rosa hybrida* Floribunda rose plant was created by artificial pollination wherein two parents were crossed which previously had been studied in the hope that they would contribute the desired characteristics. The female parent (i.e., the seed parent) was the product of the cross at the 'Meidanu' variety (non-patented in the United States) and the 'Macev' variety (U.S. Plant Pat. No. 2,424). The 'Macev' variety sometimes is known as the 'Evelyn Fison' variety. The male parent (i.e., the pollen parent) was the 'Tantide' variety (non-patented in the United States). The 'Tantide' variety sometimes is known as the 'Glad Tidings' variety. The parentage of the new variety can be summarized as follows:

'(Meidanu'×'Macev')×'Tantide'.

The seeds resulting from the above pollination were sown and small plants were obtained which were physically and biologically different from each other. Selective study resulted in the identification of a single plant of the new variety.

It was found that the new Floribunda rose variety of the present invention (a) Exhibits a bushy and vigorous well-formed growth habit, (b) Abundantly forms on continuous basis attractive semi-double blossoms that are red spotted with white in coloration, (c) Forms very dense medium green foliage with a dull aspect that contrasts well with the blossom coloration, and (d) Is particularly well suited for growing as ornamentation in parks and gardens.

The disease resistance is good with respect to *Marsonia rosae* and Phragmidium.

The new variety well meets the needs of the horticultural industry and can be used to advantage for growing in the landscape where attractive ornamentation is desired.

The new variety of the present invention can be readily distinguished from its ancestors. For instance, the flowers of the 'Meidanu' variety are of a darker and more uniform coloration, the flowers of the 'Macev' variety also lack bicoloration, and 'Tantide' variety exhibits darker foliage and a taller growth habit.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meicinelle' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately eighteen months of age and were observed during June while budded on *Rosa froebelli* understock and growing outdoor at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIB. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with five leaflets—plan view—under surface; and FIG. 15—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of eighteen month-old plants during October while budded on *Rosa froebelli* understock and growing outdoors at Le Cannet des Maures, Var, France.

Class: Floribunda.

Plant:

*Height.*—Approximately 70 to 80 cm on average at the end of the growing season.

*Width.*—Approximately 80 to 100 cm on average at the end of the growing season.

*Habit.*—Bushy.

Branches:

*Color.*—Young stems: near Yellow-Green Group 147C suffused with Greyed-Red Group 179A. Adult wood: near Yellow-Green Group 148A.

*Thorns.*—Size: variable (as illustrated). Quantity: on 10 cm of young stems approximately 7 on average greater than 5 mm in length and approximately 8 on average less than 5 mm in length, and on 10 cm of mature stems approximately 8 greater than 5 mm in length. Color: near Yellow-Green Group 147C suffused with Greyed-Red Groups 179A on young stems and near Greyed-Orange Group 174A to 174B on adult wood. Configuration: curved downwards on the upper surface and concave under surface.

Leaves:

*Stipules.*—Adnate, pectinate, and rather broad.

*Petioles.*—Upper surface: non-glandular, dark green, near Yellow-Green Group 147A. Under surface: near Yellow-Green Group 147B with a few prickles. Length: approximately 2 cm on average with the terminal leaflet.

*Leaflets.*—Number: 3, 5, and 7 (most often). shape: somewhat ovate with an obtuse base and a cuspidate tip. Size: terminal leaflets commonly measure approximately 5 cm in length and approximately 4 cm in width on average. Serration: simple and regular (as illustrated). Texture: leathery. General appearance: very dense, and medium dark green with a dull aspect. Color (young foliage): upper surface: near Yellow-Green Group 146A. under surface: near Yellow-Green Group 146C. Color (adult foliage): upper surface: near Yellow-Green Group 147A. under surface: near Yellow-Green Group 147C.

Inflorescence:

*Number of flowers.*—Singly and commonly in flat clusters of 2 to 5 flowers per stem.

*Peduncle.*—Glandular with a few tiny prickles, near Yellow-Green Group 147B and 147C suffused with Greyed-Red Group 178B, and the length is approximately 4 cm on average.

*Sepals.*—Upper surface: tomentose and near Yellow-Green Group 147C in coloration. Under surface: glandular, and near Yellow-Green 147A and 147B suffused with Greyed-Red Group 178B in coloration. Configuration: elongated and commonly without extensions (as illustrated).

*Buds.*—Shape: conical. Size: small (as illustrated). Length: approximately 2 cm on average. Color: upper surface: as the calyx breaks velvety red, near Red Group 45A and spotted with Yellow-White Group 158C. under surface: new Yellow-White 158B and widely suffused with Red Group 55A. Basal petal spot: near Yellow Group 4D on upper and under surfaces.

*Flower.*—Shape: flat cup-shaped. Diameter: approximately 7 to 8 cm on average. Color (when blooming): upper surface: velvety, near Red Group 45A with some spots of Yellow-White Group 158C suffused with Red Group 45A. under surface: Yellow-White Group 158B and widely suffused with Red Group 55A. Basal petal spot: Yellow Group 4D Fragrance: none. Lasting quality: long, the blossoms commonly last approximately 10 days on the plant on average. Petal number: approximately 19 to 20 average under normal growing conditions. Petal shape: rounded at the tip and somewhat pointed at the base with slight undulation and commonly without reflexed margins. Petal texture: thick. Petal arrangement: imbricated. Petal drop: good with the petals commonly detaching cleanly. Stamen number: approximately 141 on average. Anthers: regularly arranged around the styles, and near Yellow-Orange Group 17A in coloration. Pollen: present and yellow in coloration. Filaments: near Yellow-Orange Group 17D in coloration. Pistils: approximately 139 on average. Stigmas: near Yellow-Orange Group 19D. Styles: near Yellow-Orange Group 19C in coloration. Receptacle: glandular, near Yellow-Green Group 147B and 147C suffused with Greyed-Red Group 178B in coloration, and funnel-shaped in longitudinal section. Hips: generally round in configuration.

Development:

*Vegetation.*—Strong.

*Blooming.*—Very abundant and continuous.

*Resistance to diseases.*—Good with respect to *Marsonia rosae* and Phragmidium.

*Aptitude to bear fruit.*—Good.

I claim:

1. A new and distinct variety of Floribunda rose plant characterized by the following combination of characteristics:

(a) exhibits a bushy and vigorous well-formed growth habit, (b) abundantly forms on a continuous basis attractive semi-double blossoms that are red spotted with white in coloration, (c) forms very dense medium green foliage with a dull aspect that contrasts well with the blossom coloration, and (d) is particularly well suited for growing as ornamentation in parks and gardens;

substantially as herein shown and described.

* * * * *

MEIDWELLE